(12) United States Patent
Hood et al.

(10) Patent No.: US 7,018,377 B2
(45) Date of Patent: Mar. 28, 2006

(54) METHOD AND APPARATUS FOR MODIFICATIONS OF VISUAL ACUITY BY THERMAL MEANS

(75) Inventors: Larry L. Hood, Laguna Hills, CA (US); Antonio G. Mendez, Mexicali (MX)

(73) Assignee: Refractec, Inc., Irvine, CA (US)

( * ) Notice: Subject to any disclaimer, the term of this patent is extended or adjusted under 35 U.S.C. 154(b) by 299 days.

(21) Appl. No.: 10/301,113

(22) Filed: Nov. 20, 2002

(65) Prior Publication Data

US 2004/0049186 A1 Mar. 11, 2004

Related U.S. Application Data

(60) Division of application No. 09/239,060, filed on Jan. 26, 1999, now abandoned, which is a continuation of application No. 08/957,911, filed on Oct. 27, 1997, now Pat. No. 6,213,997, which is a continuation-in-part of application No. 08/287,657, filed on Aug. 9, 1994, now Pat. No. 5,749,871.

(51) Int. Cl.
*A61F 9/007* (2006.01)

(52) U.S. Cl. .............. 606/5; 606/41; 606/50
(58) Field of Classification Search ............. 606/5, 606/41–50
See application file for complete search history.

(56) References Cited

U.S. PATENT DOCUMENTS

| | | | | |
|---|---|---|---|---|
| 4,381,007 A | * | 4/1983 | Doss | 606/5 |
| 4,907,585 A | * | 3/1990 | Schachar | 606/28 |
| 5,019,076 A | * | 5/1991 | Yamanashi et al. | 606/45 |

FOREIGN PATENT DOCUMENTS

WO 9315664 * 8/1993 ............ 606/47

* cited by examiner

*Primary Examiner*—David M. Shay
(74) *Attorney, Agent, or Firm*—Ben J. Yorks; Irell & Manella LLP (57) ABSTRACT

A thermokeratoplasty system and method for locally heating and reshaping a cornea in a manner that produces a minimal regression of the corneal correction. The system includes a probe that is coupled to a power source which can provide current at a predetermined power, frequency and time duration. The probe has a sharp tip that is inserted into the stroma of the cornea. The tip has an insulated stop that controls the depth of tip penetration. Current flows into the cornea through the probe tip to locally heat and denature the corneal tissue. The denatured tissue causes a subsequent shrinkage of the cornea. A pattern of denatured areas can be created around the cornea to correct the vision of the eye.

3 Claims, 11 Drawing Sheets

METHOD AND APPARATUS FOR MODIFICATIONS OF VISUAL ACUITY BY THERMAL MEANS

CROSS-REFERENCES TO RELATED APPLICATIONS

This application is a divisional of application Ser. No. 09/239,060, filed on Jan. 26, 1999, now abandoned which is a continuation of application Ser. No. 08/957,911, filed on Oct. 27, 1997, U.S. Pat. No. 6,213,997, which is a continuation-in-part of application Ser. No. 08/287,657, filed on Aug. 9, 1994, U.S. Pat. No. 5,749,871.

BACKGROUND OF THE INVENTION

1. Field of the Invention

The present invention relates to a thermokeratoplasty probe that is placed into direct contact with the outer surface of the cornea.

2. Description of Related Art

Techniques for correcting vision have included reshaping the cornea of the eye. For example, myopic conditions can be corrected by cutting a number of small incisions in the corneal membrane. The incisions allow the corneal membrane to relax and increase the radius of the cornea. The incisions are typically created with either a laser or a precision knife. The procedure for creating incisions to correct myopic defects is commonly referred to as radial keratotomy and is well known in the art.

Present radial keratotomy techniques generally make incisions that penetrate approximately 95% of the cornea. Penetrating the cornea to such a depth increases the risk of puncturing the decemets membrane and the endothelium layer, and creating permanent damage to the eye. Additionally, light entering the cornea at the incision sight is refracted by the incision scar and produces a glaring effect in the visual field. The glare effect of the scar produces impaired night vision for the patient. It would be desirable to have a procedure for correcting myopia that does not require a 95% penetration of the cornea.

The techniques of radial keratotomy are only effective in correcting myopia. Radial keratotomy cannot be used to correct an eye condition such as hyperopia. Additionally, keratotomy has limited use in reducing or correcting an astigmatism. The cornea of a patient with hyperopia is relatively flat (large spherical radius). A flat cornea creates a lens system which does not correctly focus the viewed image onto the retina of the eye. Hyperopia can be corrected by reshaping the eye to decrease the spherical radius of the cornea. It has been found that hyperopia can be corrected by heating and denaturing local regions of the cornea. The denatured tissue contracts and changes the shape of the cornea and corrects the optical characteristics of the eye. The procedure of heating the corneal membrane to correct a patient's vision is commonly referred to as thermokeratoplasty.

U.S. Pat. No. 4,461,294 issued to Baron; U.S. Pat. No. 4,976,709 issued to Sand and PCT Publication WO 90/12618, all disclose thermokeratoplastic techniques which utilize a laser to heat the cornea. The energy of the laser generates localized heat within the corneal stroma through photonic absorption. The heated areas of the stroma then shrink to change the shape of the eye.

Although effective in reshaping the eye, the laser based systems of the Baron, Sand and PCT references are relatively expensive to produce, have a non-uniform thermal conduction profile, are not self limiting, are susceptible to providing too much heat to the eye, may induce astigmatism and produce excessive adjacent tissue damage, and require long term stabilization of the eye. Expensive laser systems increase the cost of the procedure and are economically impractical to gain widespread market acceptance and use. Additionally, laser thermokeratoplastic techniques non-uniformly shrink the stroma without shrinking the Bowmans layer. Shrinking the stroma without a corresponding shrinkage of the Bowmans layer, creates a mechanical strain in the cornea. The mechanical strain may produce an undesirable reshaping of the cornea and probable regression of the visual acuity correction as the corneal lesion heals. Laser techniques may also perforate Bowmans layer and leave a leucoma within the visual field of the eye.

U.S. Pat. Nos. 4,326,529 and 4,381,007 issued to Doss et al, disclose electrodes that are used to heat large areas of the cornea to correct for myopia. The electrode is located within a housing that spaces the tip of the electrode from the surface of the eye. An isotropic saline solution is irrigated through the electrode and aspirated through a channel formed between the outer surface of the electrode and the inner surface of the sleeve. The saline solution provides an electrically conductive medium between the electrode and the corneal membrane. The current from the electrode heats the outer layers of the cornea. Heating the outer eye tissue causes the cornea to shrink into a new radial shape. The saline solution also functions as a coolant which cools the outer epithelium layer.

The saline solution of the Doss device spreads the current of the electrode over a relatively large area of the cornea. Consequently, thermokeratoplasty techniques using the Doss device are limited to reshaped corneas with relatively large and undesirable denatured areas within the visual axis of the eye. The electrode device of the Doss system is also relatively complex and cumbersome to use.

"A Technique for the Selective Heating of Corneal Stroma" Doss et al., Contact & Intraoccular Lens Medical Jrl., Vol. 6, No. 1, pp. 13–17, January-March, 1980, discusses a procedure wherein the circulating saline electrode (CSE) of the Doss patent was used to heat a pig cornea. The electrode provided 30 volts r.m.s. of power for 4 seconds. The results showed that the stroma was heated to 70° C. and the Bowman's membrane was heated 45° C., a temperature below the 50–55° C. required to shrink the cornea without regression.

"The Need For Prompt Prospective Investigation" McDonnell, Refractive & Corneal Surgery, Vol. 5, January/February, 1989 discusses the merits of corneal reshaping by thermokeratoplasty techniques. The article discusses a procedure wherein a stromal collagen was heated by radio frequency waves to correct for a keratoconus condition. As the article reports, the patient had an initial profound flattening of the eye followed by significant regression within weeks of the procedure.

"Regression of Effect Following Radial Thermokeratoplasty in Humans" Feldman et al., Refractive and Corneal Surgery, Vol. 5, September/October, 1989, discusses another thermokeratoplasty technique for correcting hyperopia. Feldman inserted a probe into four different locations of the cornea. The probe was heated to 600° C. and was inserted into the cornea for 0.3 seconds. Like the procedure discussed in the McDonnell article, the Feldman technique initially reduced hyperopia, but the patients had a significant regression within 9 months of the procedure. To date, there has been no published findings of a thermokeratoplasty technique that will predictably reshape and correct the vision of a cornea without a significant regression of the corneal correction.

It would therefore be desirable to provide a thermokeratoplasty technique which can predictably reshape and correct the vision of an eye without a significant regression of the visual acuity correction.

Electrodes are subject to contamination, when RF electrical current is used for thermokeratoplasty. For example, an electrolyzed layer or protein film may form on the surface of the electrodes. Such a film may vary the impedance of the electrodes and affect the performance of the instrument. Varying instrument performance may create inconsistent results. Therefore it would be desirable to provide a thermokeratoplastic probe that would have to be replaced by a new device after a predetermined number of uses.

SUMMARY OF THE INVENTION

The present invention is a thermokeratoplasty system and method for locally heating and reshaping a cornea in a manner that produces a minimal regression of the corneal correction. The system includes a probe that is coupled to a power source which can provide current at a predetermined power, frequency and time duration. The probe has a sharp tip that is inserted into the stroma of the cornea. The tip has an insulated stop that controls the depth of tip penetration. Current flows into the cornea through the probe tip to locally heat and denature the corneal tissue. The denatured tissue causes a subsequent shrinkage of the cornea. A pattern of denatured areas can be created around the cornea to correct the vision of the eye.

BRIEF DESCRIPTION OF THE DRAWINGS

The objects and advantages of the present invention will become more readily apparent to those ordinarily skilled in the art after reviewing the following detailed description and accompanying drawings, wherein.

DETAILED DESCRIPTION OF TRE INVENTION

Figure 1:
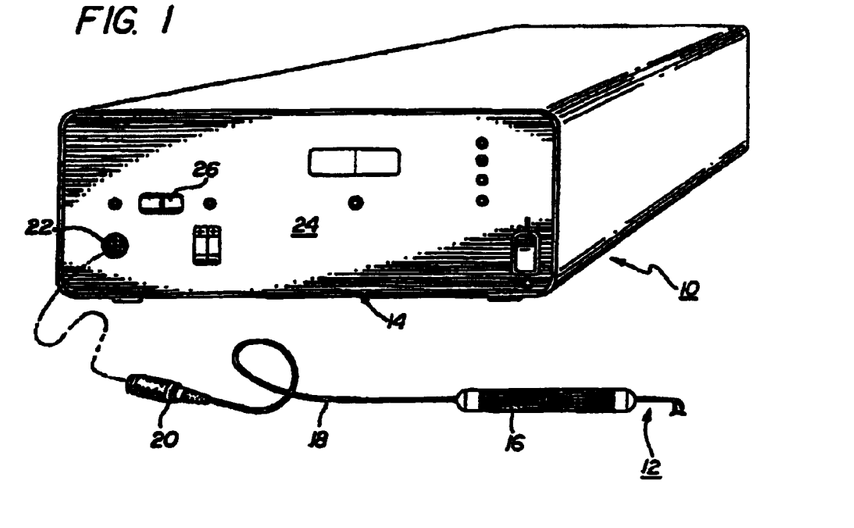
FIG. 1 is a perspective view of a thermokeratoplastic electrode system of the present invention.

Referring to the drawings more particularly by reference numbers, FIG. 1 shows a thermokeratoplastic electrode system 10 of the present invention. The system 10 includes an electrode probe 12 coupled to a power supply unit 14. The power supply unit 14 contains a power supply which can deliver power to the probe 12. The probe 12 has a hand piece 16 and wires 18 that couple the probe electrodes to a connector 20 that plugs into a mating receptacle 22 located on the front panel 24 of the power unit. The hand piece 16 may be constructed from a non-conductive material and is approximately 0.5 inches in diameter and 5 inches long.

The power supply 14 provides a predetermined amount of energy, through a controlled application of power for a predetermined time duration. The power supply 14 may have manual controls that allow the user to select treatment parameters such as the power and time duration. The power supply 14 can also be constructed to provide an automated operation. The supply 14 may have monitors and feedback systems for measuring tissue impedance, tissue temperature and other parameters, and adjust the output power of the supply to accomplish the desired results. The unit may also have a display that indicates the number of remaining uses available for the probe 12.

In the preferred embodiment, the power supply provides a constant current source and voltage limiting to prevent arcing. To protect the patient from overvoltage or overpower, the power unit 14 may have an upper voltage limit and/or upper power limit which terminates power to the probe when the output voltage or power of the unit exceeds a predetermined value. The power unit 14 may also contain monitor and alarm circuits which monitor the resistance or impedance of the load and provide an alarm when the resistance/impedance value exceeds and/or falls below predefined limits. The alarm may provide either an audio and/or visual indication to the user that the resistance/impedance value has exceeded the outer predefined limits. Additionally, the unit may contain a ground fault indicator, and/or a tissue temperature monitor. The front panel of the power unit typically contains meters and displays that provide an indication of the power, frequency, etc., of the power delivered to the probe.

Figure 1A:
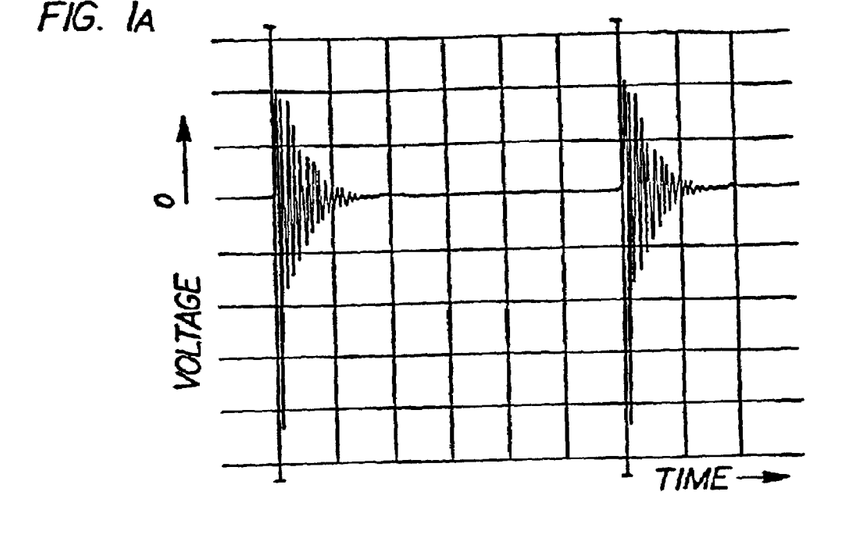
FIG. 1a is a graph showing a waveform that is provided to the probe of the system.

The power unit 14 may deliver a power output in a frequency range of 5 KHz–50 MHz. In the preferred embodiment, power is provided to the probe at a frequency in the range of 500 KHz. The unit 14 is designed so that the power supplied to the probe 12 does not exceed 1.2 watts (W). The time duration of each application of power to a particular corneal location is typically between 0.1–1.0 seconds. The unit 14 is preferably set to deliver approximately 0.75 W of power for 0.75 seconds. FIG. 1a shows a typical voltage waveform that is applied by the unit 14. Each pulse of energy delivered by the unit 14 is a highly damped signal, typically having a crest factor (peak voltage/RMS voltage) greater than 10:1. Each power dissipation is provided at a repetitive rate. The repetitive rate may range between 4–12 KHz and is preferably set at 8 KHz.

The system has a switch which controls the application of power to the probe 12. The power unit 14 also contains a timer circuit which allows power to be supplied to the probe 12 for a precise predetermined time interval. The timer may be a Dose timer or other similar conventional circuitry which terminates power to the probe after a predetermined time interval. The unit may also allow the user to apply power until the switch is released. As one embodiment, the power supply may be a unit sold by Birtcher Medical Co. under the trademark HYFRECATOR PLUS, Model 7-797 which is modified to have voltage, waveform, time durations and power limits to comply with the above cited specifications.

The power unit 14 may have a control member 26 to allow the user to select between a "uni-polar" or a "bi-polar" operation. The power supply 14 may be constructed to provide a single range of numerical settings, whereupon the appropriate output power, time duration and repetition rate are determined by the hardware and software of the unit. The front panel of the power unit may also have control members (not shown) that allow the surgeon to vary the power, frequency, timer interval, etc. of the unit. The return electrode (not shown) for a uni-polar probe may be coupled to the power unit through a connector located on the unit. The return electrode is preferably a cylindrical bar that is held by the patient, or an eye fixation electrode.

It has been found that at higher diopters, effective results can be obtained by providing two different applications at the same location. Listed below in Table I are the power settings (peak power) and time duration settings for different diopter corrections (−d), wherein the locations (Loc) are the number of denatured areas in the cornea and dots/Loc is the number of power applications per location.

TABLE I

| −d | DOTS/LOC | LOC | PWR (W) | TIME (SEC) |
|---|---|---|---|---|
| 1.5 | 1 | 8 | 0.66 | .75 |
| 2.5 | 2 | 8 | 0.66 | .75 |
| 3.5 | 2 | 8 | 0.83 | .75 |
| 4.5 | 2 | 16 | 0.66 | .75 |
| 6.0 | 2 | 16 | 0.83 | .75 |

Figure 1B:
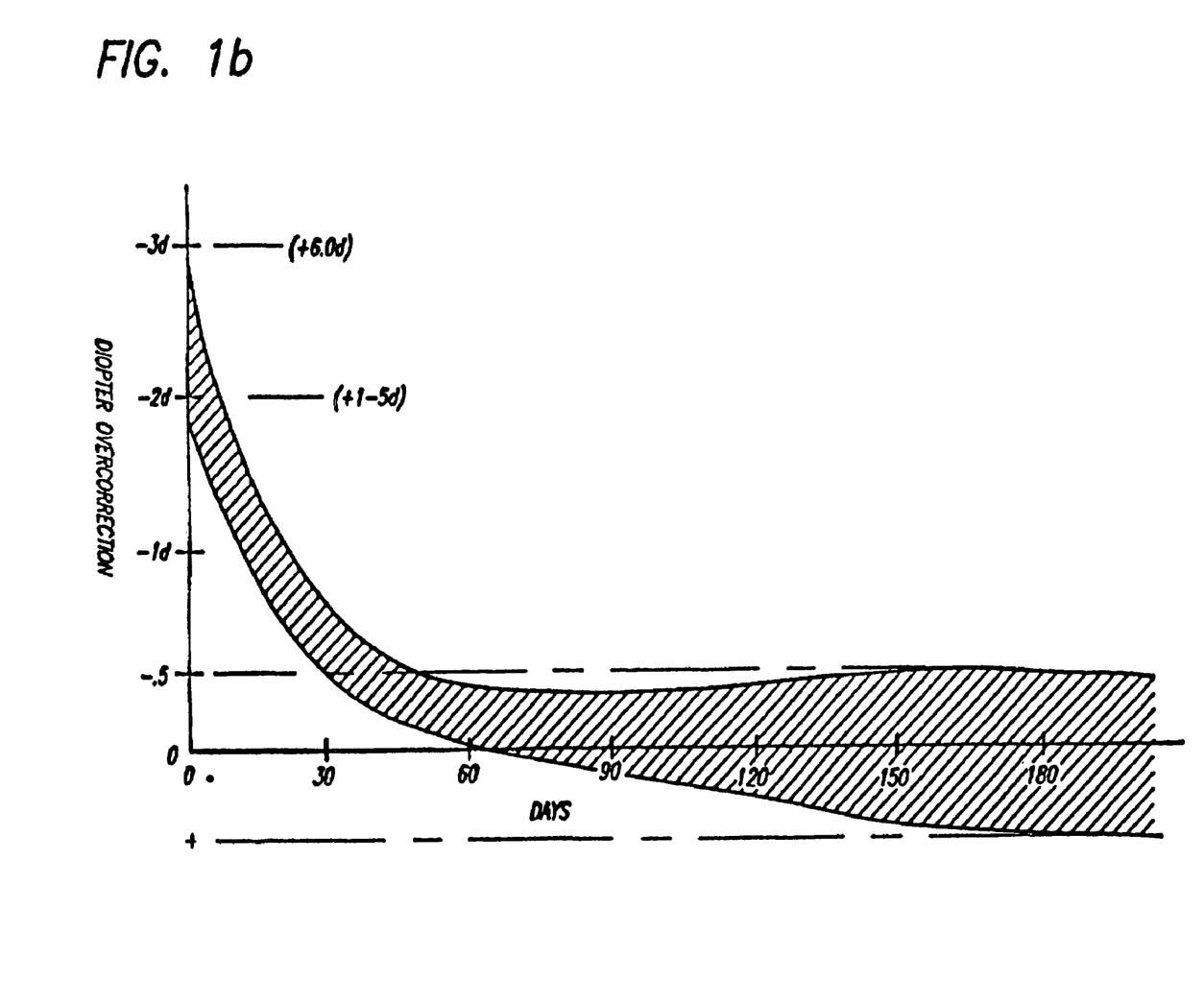
FIG. 1b is a graph showing the amount of typical vision correction regression over time.

Using the parameters listed in Table I, the procedure of the present invention was performed on 36 different patients suffering from some degree of hyperopia. A pattern of 8–16 denatured areas were created in the non-vision area of the eye. Patients who needed higher diopter corrections were treated with high applications of power. FIG. 1b shows the amount of regression in the vision correction of the eye. The eyes were initially overcorrected to compensate for the known regression in the procedure. As shown in FIG. 1b, the regression became stabilized after approximately 60 days and completely stabilized after 180 days. The error in overcorrection was within +/−0.5 diopters.

Figure 1C:
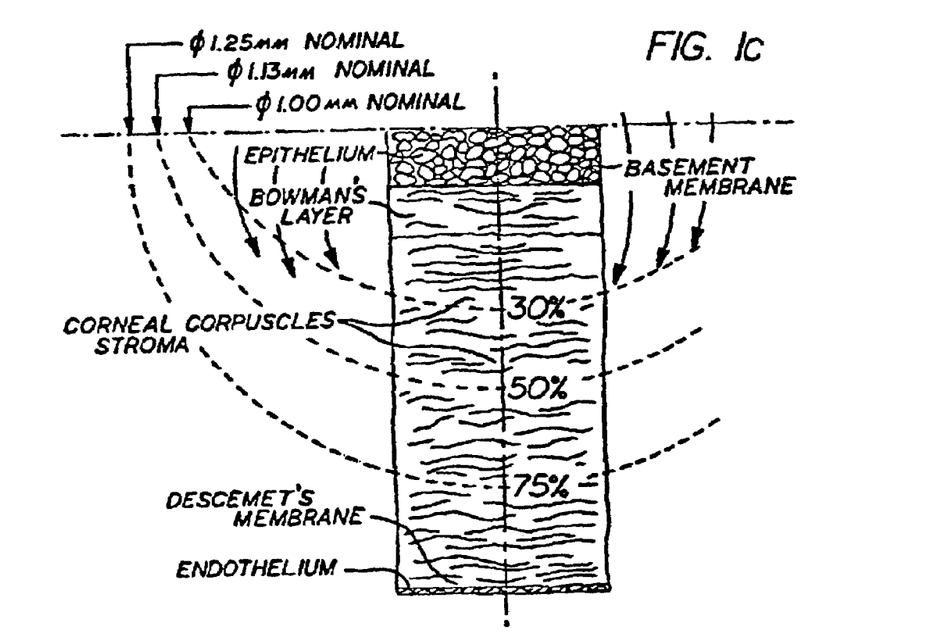
FIG. 1c is a representation of a nominal thermal profile within the cornea produced by the electrode system of the present invention.

FIG. 1c shows nominal thermal profiles produced by the application of power to the cornea. As known to those skilled in the art, the cornea includes an epithelium layer, a Bowmans membrane, a stroma, a Descemets membrane and a endothelium layer. Without limiting the scope of the patent, the applicant provides the following discussion on the possible effects of the present method on the cornea of the eye. When power is first applied to the cornea the current flows through the center of the tissue immediately adjacent to the probe tip. The application of power causes an internal ohmic heating of the cornea and a dehydration of the tissue. The dehydration of the tissue rapidly increases the impedance of the local heated area, wherein the current flows in an outward manner indicated by the arrows in FIG. 1c. The cycle of dehydration and outward current flow continues until the resistance from the tip to the outer rim of the corneal surface, and the full thermal profile, is significantly high to prevent further current flow of a magnitude to further cause denaturing of the corneal tissue. The direct contact of the probe with the cornea along the specific power/time settings of the power source creates a thermal profile that denatures both the Bowman's membrane and the stroma. The denaturing of both the Bowman's membrane and the stroma in a circular pattern creates a linked belt type contracted annular ring. This annular ring will create a steepening of the cornea and sharpen the focus of the images on the retina. To control and minimize the denatured area, the surface of the eye is kept dry by applying either a dry swab to the cornea or blowing dry air or nitrogen across the surface of the eye.

The design of the power source and the high electrical resistance of the denatured area provides a self limit on the amount of penetration and area of denaturing of the cornea. Once denatured, the cornea provides a high impedance to any subsequent application of power so that a relatively low amount of current flows through the denatured area. It has been found that the present procedure has a self limited denatured profile of approximately no greater than 75% of the depth of the stroma. This prevents the surgeon from denaturing the eye down to the decemets membrane and endothelium layer of the cornea.

FIG. 1c shows nominal thermal profiles for diopter corrections of −1.5 d, −2.5–3.5 d and −4.0–6.0 d, respectively. In accordance with Table I, a −1.5 diopter correction creates a denatured diameter of approximately 1 mm and a stroma penetration of approximately 30%. A −2.5–3.5 d correction creates a denatured diameter of approximately 1.13 mm and a stroma penetration of approximately 50%. A −4.0–6.0 d correction creates a denature diameter of approximately 1.25 mm and a stroma penetration of approximately 75%.

FIGS. 2–5 show an embodiment of the probe 12. The probe 12 has a first electrode 30 and a second electrode 32. Although two electrodes are described and shown, it is to be understood that the probe may have either both electrodes (bipolar) or just the first electrode (unipolar). If a unipolar probe is used, a return electrode (indifferent electrode) is typically attached to, or held by, the patient to provide a "return" path for the current of the electrode.

Both electrodes 30 and 32 extend from the hand piece 16 which contains a pair of internal insulated conductors 34 that are contact with the proximal end of the electrodes. The first electrode 30 has a tip 36 which extends from a first spring member 38 that is cantilevered from the hand piece 16. The electrode 30 is preferably constructed from a phosphorbronze or stainless steel, wire or tube, that is 0.2–1.5 mm in diameter. The spring portion 38 of the first electrode 30 is preferably 50 millimeters (mm) long. In one embodiment, the tip 36 has an included angle of between 15–60°, 30° nominal, and a nose radius of approximately 50 microns. A majority of the electrode 30 is covered with an insulating material to prevent arcing, and to protect non-target tissue, the user and the patient. The relatively light spring force of the probe provides a sufficient electrode pressure without penetrating the cornea.

Figure 2:
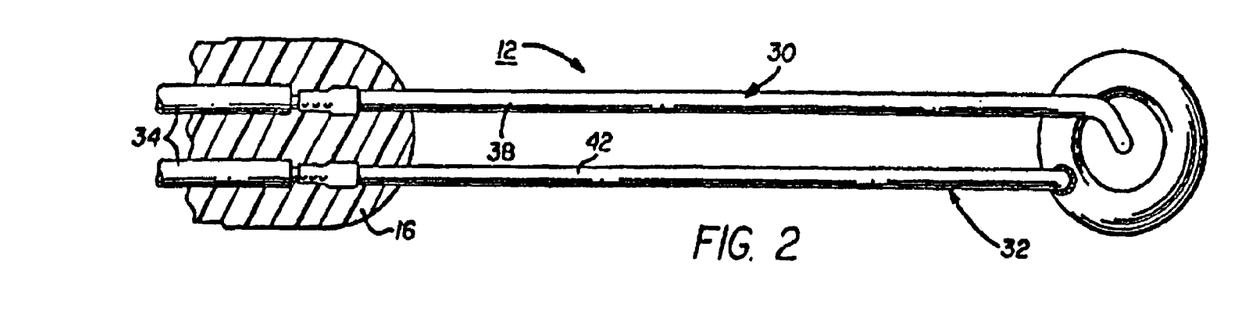
FIG. 2 is a top view of an electrode probe of the system.
Figure 3:
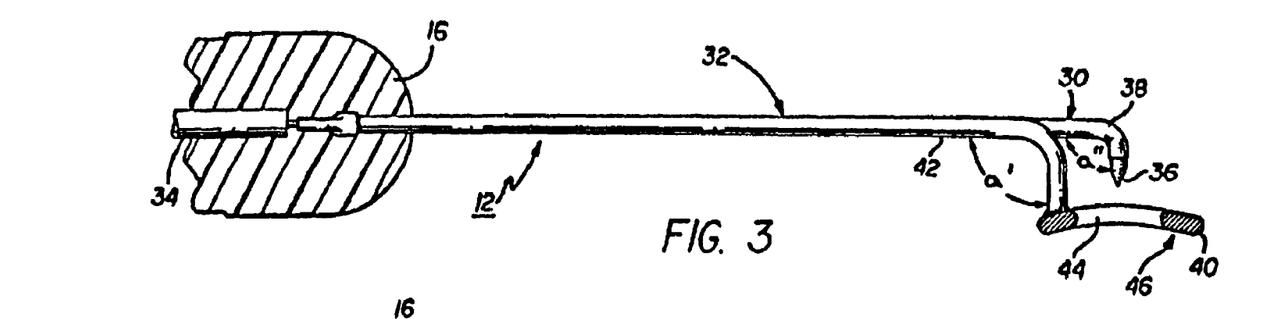
FIG. 3 is a side view of the probe in FIG. 2.

The second electrode 32 includes a disk portion 40 which extends from a second spring member 42 that is also cantilevered from the hand piece 16. The disk portion 40 is spaced a predetermined distance from first electrode 30 and has an aperture 44 that is concentric with the tip 36. In the preferred embodiment, the disk portion 40 has an outer diameter of 5.5 mm and an aperture diameter of 3.0 mm. The disk 40 further has a concave bottom surface 46 that generally conforms to the shape of the cornea or sclera.

Figure 5:
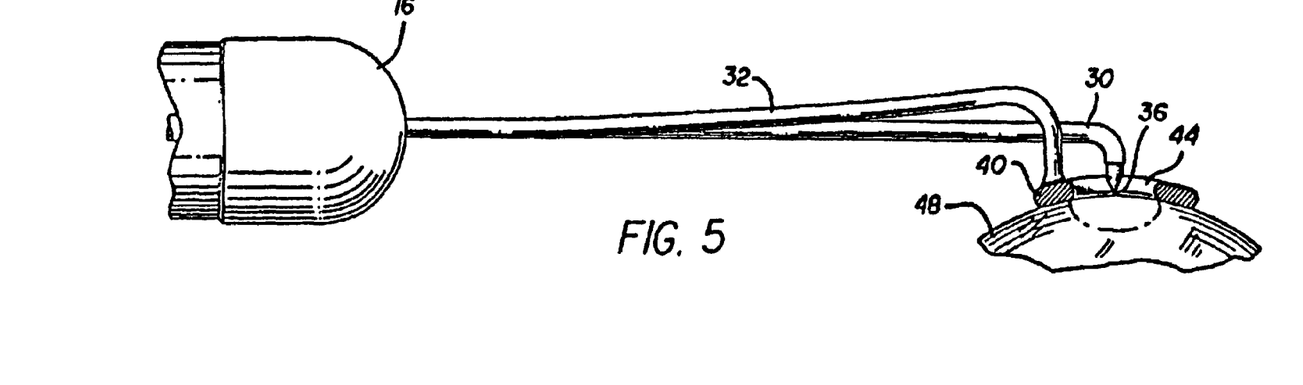
FIG. 5 is a side view showing the probe being used to treat an area of the corneal membrane.

In one embodiment, the bottom surface 46 has a spherical radius of approximately 12.75 mm and a griping surface to assist in the fixation of the eye. The second electrode 32 provides a return path for the current from the first electrode 30. To insure proper grounding of the cornea, the surface area of the disk 40 is typically 20–500 times larger than the contact area of the tip 36. In the preferred embodiment, the second spring member 42 is constructed to have a spring constant that is less than one-half the stiffness of the first spring member 38, so that the second electrode 32 will have a greater deflection per unit force than the first electrode 30. As shown in FIG. 3, the tip 36 and disk 40 are typically located at angles a' and a" which may range between 30°–180°, with the preferred embodiment being 45°. As shown in FIG. 5, the probe 12 is pressed against the cornea to allow the second electrode 32 to deflect-relative to the first electrode 30. The second electrode 32 is deflected until the tip 36 is in contact with the cornea.

For surgeons who prefer "two handed" procedures, the probe could be constructed as two pieces, one piece being the first electrode, and the other piece being the second electrode which also stabilizes the eye against corneal movement. Although the probe has been described and shown denaturing a cornea, it is to be understood that the probes and methods of the present invention can be used to denature other tissues to correct for wrinkles, incontinence, etc. For example, the probe could be used to shrink a sphincter to correct for incontinence. The technique would be basically the same with small closely spaced dots forming a tightening line, belt or cylinder.

Figure 6:
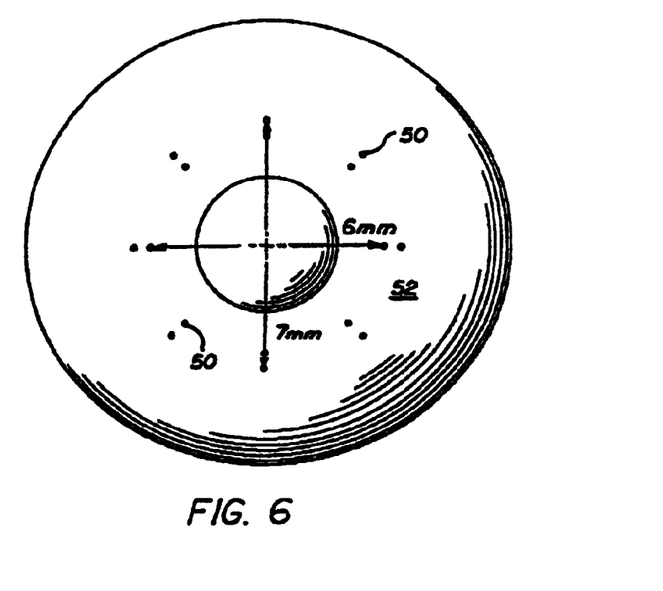
FIG. 6 is a top view showing a pattern of denatured areas of the cornea.

FIG. 6 shows a pattern of denatured areas 50 that have been found to correct hyperopic conditions. A circle of 8 or 16 denatured areas 50 are created about the center of the cornea, outside the visual axis portion 52 of the eye. The visual axis has a nominal diameter of approximately 5 millimeters. It has been found that 16 denatured areas provide the most corneal shrinkage and less post-op astigmatism effects from the procedure. The circle of denatured areas typically have a diameter between 6–8 mm, with a preferred diameter of approximately 7 mm. If the first circle does not correct the eye deficiency, the same pattern may be repeated, or another pattern of 8 denatured areas may be created within a circle having a diameter of approximately 6.0–6.5 mm either in line or overlapping. It has been found that overcorrected hyperopic conditions may be reversed up to 80% by applying a steroid, such as cortisone, to the denatured areas within 4 days of post-op and continued for 2 weeks after the procedure. The procedure of the present invention can then be repeated after a 30 day waiting period.

The exact diameter of the pattern may vary from patient to patient, it being understood that the denatured spots should preferably be formed in the non-visionary portion 52 of the eye. Although a circular pattern is shown, it is to be understood that the denatured areas may be located in any location and in any pattern. In addition to correcting for hyperopia, the present invention may be used to correct astigmatic conditions. For correcting astigmatic conditions, the denatured areas are typically created at the end of the astigmatic flat axis. The present invention may also be used to correct radial keratotomy procedures that have overcorrected for a myopic condition.

The probe and power settings have been found to create denatured areas that do not reach the Decemets membrane. It has been found that denatured areas of the Bowmans layer in the field of vision may disturb the patients field of vision, particularly at night. The present invention leaves a scar that is almost imperceptible by slit lamp examination 6 months after the procedure. It has been found that the denatured areas generated by the present invention do not produce the star effect caused by the refraction of light through the slits created in a corrective procedure such as radial keratotomy.

Figures 4, 7:
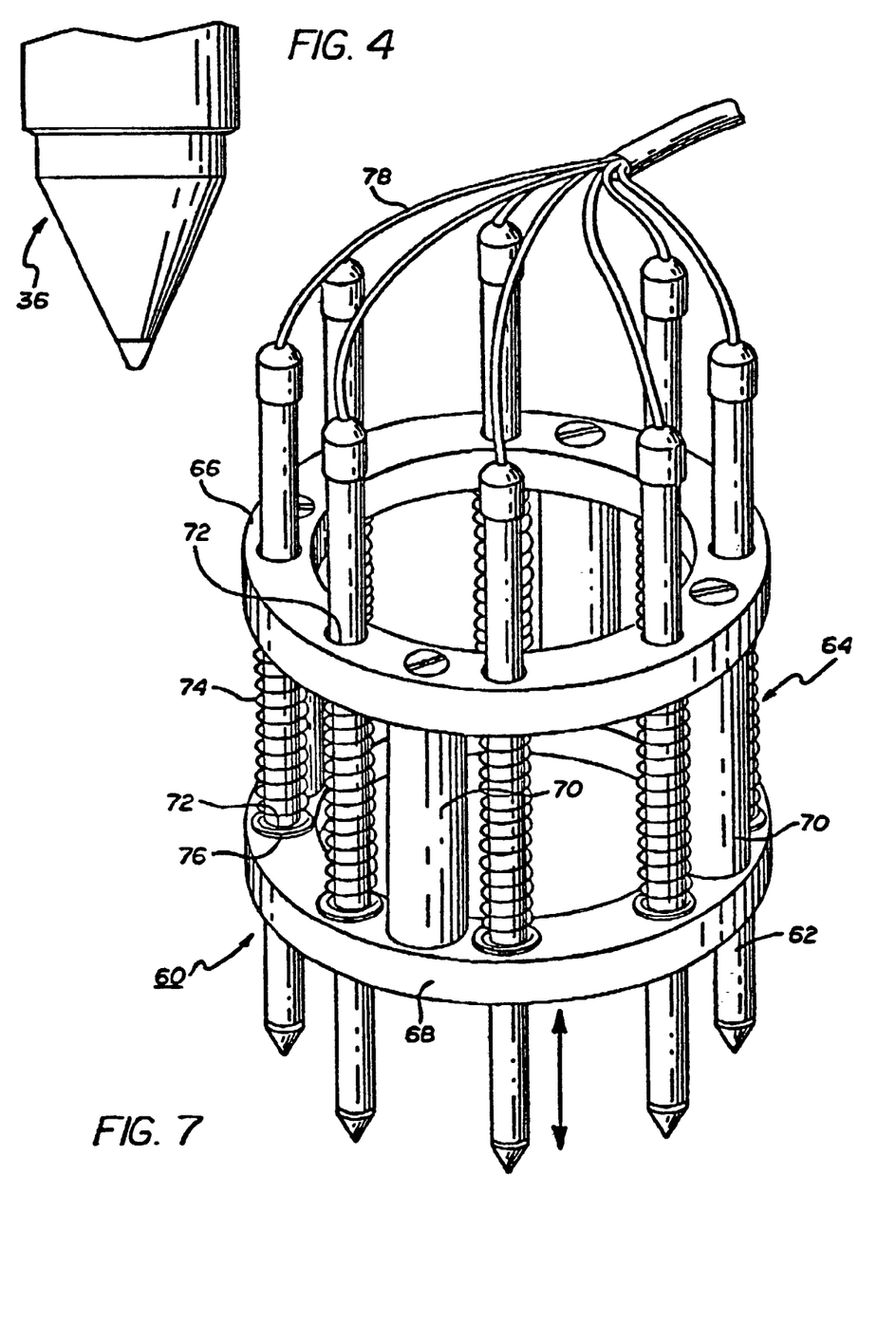
FIG. 4 is an enlarged view of the probe tip.
FIG. 7 is a perspective view of an alternate embodiment of the probe.

FIG. 7 shows an alternate embodiment of a probe 60 which has a plurality of first electrodes 62 coupled to a cage 64. The cage 64 includes a first ring 66 separated from a second ring 68 by a number of spacers 70. The cage 64 can be connected to a handle (not shown) which allows the surgeon to more easily utilize the probe 60.

The first electrodes 62 extend through apertures 72 in the rings 66 and 68. The electrodes 62 can move relative to the cage 64 in the directions indicated by the arrows. The probe 60 has a plurality springs 74 located between the rings and seated on washers 76 mounted to the electrodes 62. The springs 74 bias the electrodes 62 into the positions shown in FIG. 7. In the preferred embodiment, the probe 60 includes 8 electrodes arranged in a circular pattern having a 7.0 millimeter diameter.

In operation, the probe 60 is pressed onto the cornea so that the electrodes 62 move relative to the cage 64. The spring constant of the springs 74 is relatively low so that there is a minimal counterforce on the tissue. A current is supplied to the electrodes 62 through wires 78 attached thereto. The probe 60 is preferably used as a uni-polar device, wherein the current flows through the tissue and into a return electrode attached to or held by the patient.

Figure 8A:
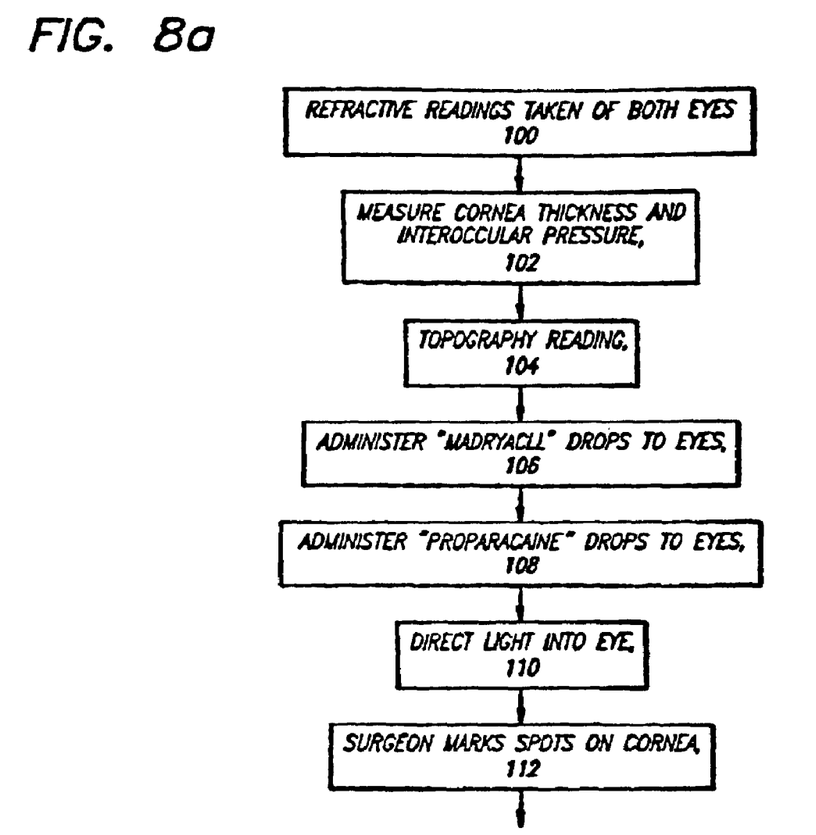
FIGS. 8a–b show a method for performing a procedure of the present invention.
Figure 8B:
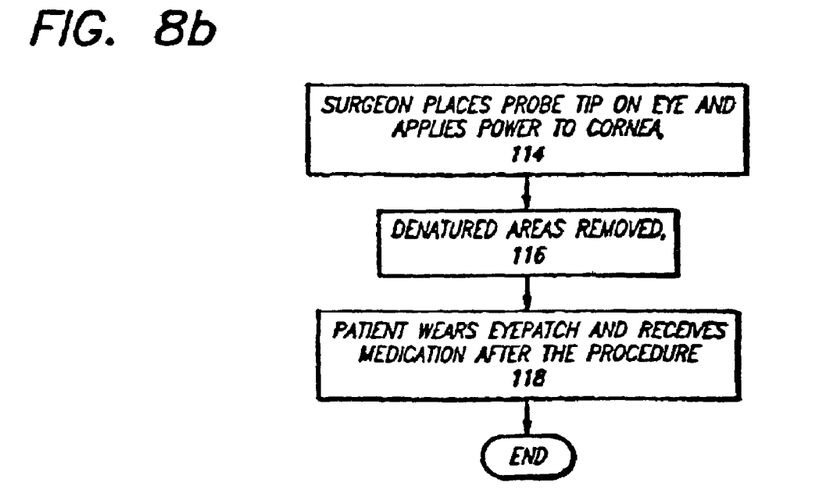

FIGS. 8a and 8b show a preferred method of correcting for hyperopic conditions using the electrode system of the present invention. As shown in procedural block 100 refractive readings are initially taken of both eyes with, and then without, cycloplasia. In procedure block 102, the interoccular pressure and cornea thickness at the center of the eye are taken with a tonometer and pacymeter, respectively. If the interoccular pressure is 20 mm Hg or greater, for I.O.P. reduction, 1 drop of a 0.5% solution marketed under the trademark "Betagan" is applied to the cornea twice a day for 2–3 months and then initial test are repeated. A topography reading of the eye is then taken to determine the shape of the cornea in procedural block 104.

Approximately 30 minutes before the application of the electrode, the patient is given a mild tranquilizer such as 5 mg of valium, and the surgeon administers drops, such as the drops marketed under the trademark "Madryacil", to dilate the pupil and freeze accommodation, in block 106. Immediately before the procedure, 2 drops of a topical cocaine commonly known as "Proparacaine" is administered to the eyes in block 108. In block 110 an in line microscope light is directed to the cornea for marking purposes. Then the lighting may be directed in a lateral direction across the cornea. Laterally lighting the eye has been found to provide good visualization without irritating or photobleaching the retina.

In procedural block 112, the surgeon marks 8 or 16 spots on the cornea, wherein the pattern has a preferred diameter of approximately 7 mm. The surgeon sets the power and duration setting of the power unit to the proper setting. In block 114, the surgeon then places the tip at one of the spot markings and depresses the foot switch of the system, so that power is supplied to the probe and transferred into the cornea. This process is repeated at all of the spot markings. The epithelium of the denatured areas are then removed with a spatula in block 116. If a diopter correction of −2.5–3.5 d, or −4.0–6.0 d is required the tip is again placed in contact with the spots and power is applied to the cornea to generate a deeper thermal profile in the stroma. The procedure is then checked with an autorefractor.

The eyes are covered with a patch or dark glasses, and the patient is given medication, in block 118. The patient preferably takes an antibiotic such as a drug marketed under the trademark "Tobrex" every 2 hours for 48 hours, and then 3 times a day for 5 days. The patient also preferably takes an oral analgesic, such as a drug marketed under the trademark "Dolac", 10 mg every 8 hours for 48 hours and a drug marketed under the trademark "Globaset" every 8 hours for 48 hours. If the patient has been overcorrected, the procedure can be reversed by waiting 3–4 days after the procedure and then administering to the eyes 1 drop of a steroid such as cortisone, 3 times a day for 1–2 weeks.

Figures 9, 10:
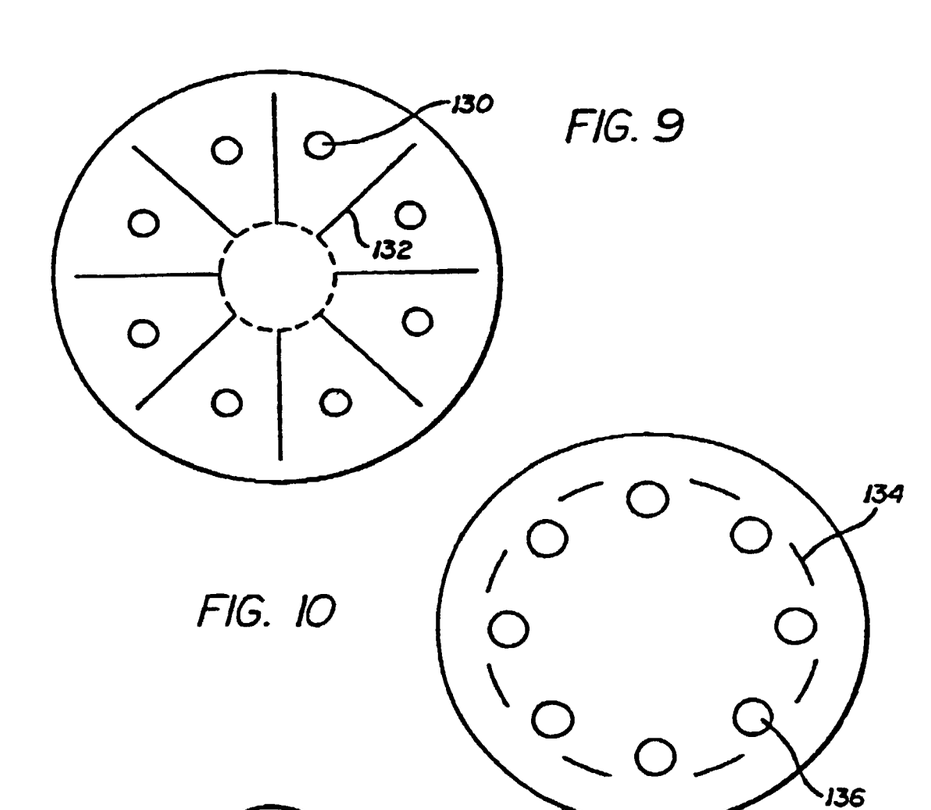
FIG. 9 shows a pattern of incisions and denatured areas to correct for a myopic condition.
FIG. 10 shows another pattern of incisions and denatured areas to correct for hyperopic conditions.

FIG. 9 shows a pattern of denatured areas 130 combined with a pattern of incisions 132 that can correct myopic conditions. The incisions can be made with a knife or laser in accordance with conventional radial keratotomy procedures. The incisions are made from a 3.5 mm diameter to within 1 mm of the limbus at a depth of approximately 85% of the cornea. Denatured areas are then created between the incisions 132 using the procedure described above. The power unit is preferably set at 0.75 W of power and a time duration of 0.75 seconds. The slow heating of the cornea is important for minimizing regression, and as such 0.75 seconds has been found to be a preferable time duration to account for the patients fixation ability and the surgeons reaction time. The denatured areas pull the incisions to assist in the reshaping of the cornea. This procedure has been found to be effective for diopter corrections up to +10.0 d. Penetrating the cornea only 85% instead of conventional keratotomy incisions of 95% reduces the risk of puncturing the decemets membrane and the endothelium layer. This is to be distinguished from conventional radial keratotomy procedures which cannot typically correct for more than 3.5 diopters.

The denatured pattern shown in FIG. 6 has been shown to correct up to 7.0 diopters. As shown in FIG. 10, a circumferential pattern of incisions 134 may be created in addition to a pattern of denatured areas 136, to increase the correction up to 10.0 diopters. The incisions will weaken the eye and allow a more pronounced reshaping of the eye. The pattern of incisions may be created at either a 6 mm diameter or a 8 mm diameter. The incisions typically penetrate no greater than 75% of the cornea. The contractive forces of the denatured areas may create gaps in the incisions. It may be preferable to fill the gaps with collagen or other suitable material.

Figure 11:
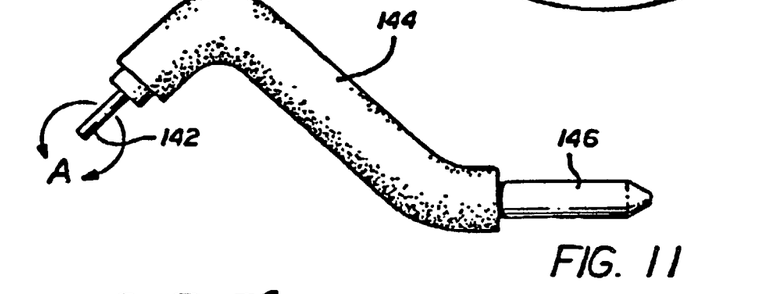
FIG. 11 shows a preferred embodiment of the present invention.

FIG. 11 shows an alternate embodiment of a probe which has a single electrode 140. The electrode 140 has a tip 142 which is preferably 0.009 inches in diameter. The tip extends from a spring beam 144 that is bent so that the surgeon can place the tip onto the cornea over nose and brow without impairing the surgeon's vision. The spring beam 144 is preferably insulated and is 0.2–1.5 mm in diameter. The spring beam 144 extends from a base 146 that is inserted into the hand piece. The base 146 is preferably constructed from stainless steel and is 0.030–0.125 inches in diameter, with a preferred diameter of 0.060–0.095 inches.

Figure 11A:
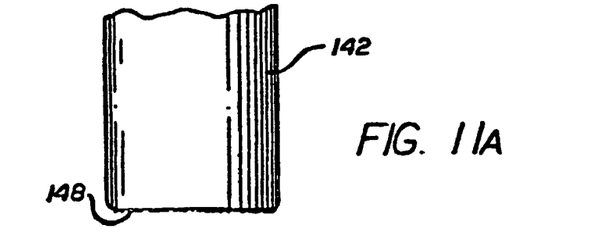
FIG. 11a is an enlarged view of the tip of FIG. 11.

As shown in FIG. 11a, the end of the tip 142 is preferably flat and has a textured surface 148. The textured surface 148 slightly grips the cornea so that the tip does not move away from the marking when power is applied to the eye.

Figures 12, 13, 14, 15:
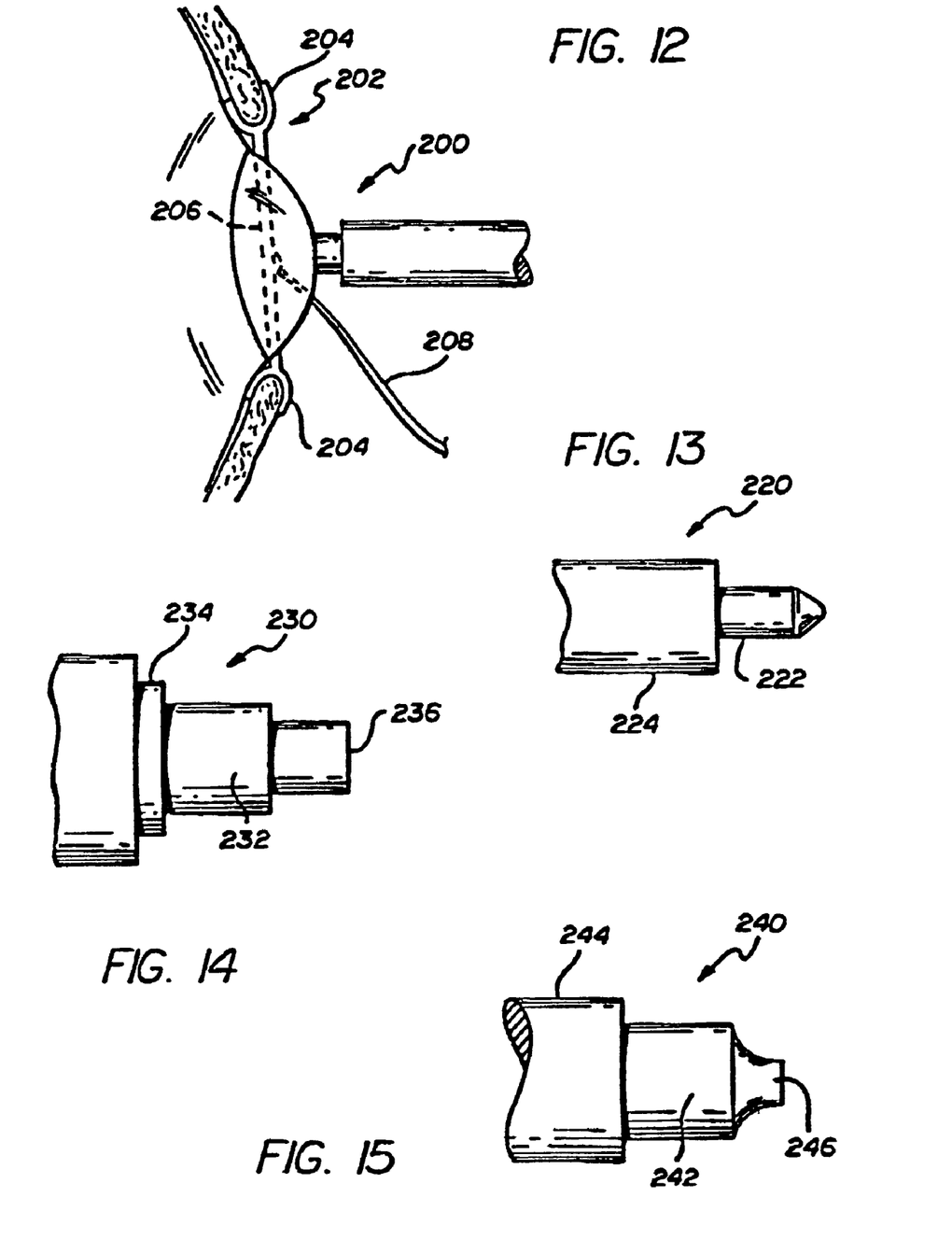
FIG. 12 is a perspective view of a probe with the return electrode as a lid speculum that maintains the eye lid in an open position.
FIG. 13 is a side view of an alternate probe tip embodiment.
FIG. 14 is a side view of an alternate probe tip embodiment.
FIG. 15 is a side view of an alternate probe tip embodiment.

As shown in FIG. 12, the probe 200 has a return electrode lid speculum 202 that maintains the eye lid in an open position. The speculum 202 has a pair of cups 204 located at the end of wire 206. The cups 204 are placed under an eye lid and maintain the position of the lid during the procedure. Extending from the lid speculum 202 is a wire 208 that is typically plugged into the unit 14 "return" connector. It has been found that the procedure of the present invention will produce more consistent results when the probe 200 uses the lid speculum 202 as the return electrode. The impedance path between the probe 200 and the lid speculum 202 is relatively consistent because of the relatively short distance between the lid speculum 202 and the probe 200, and the wet interface between the cornea and the lid speculum 202.

FIGS. 13–15 show alternate probe tip embodiments. The tips have steps that increase the current density at the corneal interface. The tips are preferably constructed from a stainless steel that is formed to the shapes shown. The tip 220 shown in FIG. 13 has a cylindrical step 222 that extends from a base 224. The step 222 terminates to a point, although it is to be understood that the end of the step 222 may have a flat surface. In the preferred embodiment, the base 224 has a diameter of 350 microns (um), and the step 222 has a diameter of 190 microns and a length of 210 microns.

The tip 230 shown in FIG. 14, has a first step 232 extending from a base portion 234 and a second step 236 extending from the first step 232. The end of the second step 236 may be textured to improve the contact between the probe and the cornea. In the preferred embodiment, the first step 232 has a diameter of 263 microns and a length of 425 microns, the second step 236 has a diameter of 160 microns and a length of 150 microns. The tip 240 shown in FIG. 15, has a first step 242 that extends from a base portion 244 and a second tapered step 246 that extends from the first step 242. In the preferred embodiment, the first step 242 has a diameter of 290 microns and a length of 950 microns. The second step 246 has a diameter of 150 microns, a length of 94 microns and a radius of 70 microns.

Figure 16:
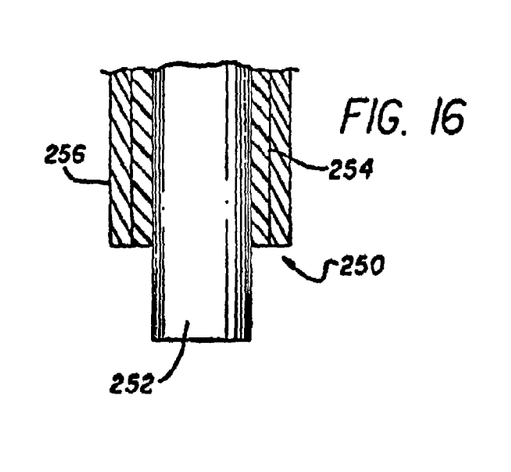
FIG. 16 is a side view of an alternate probe tip embodiment.
Figure 17:
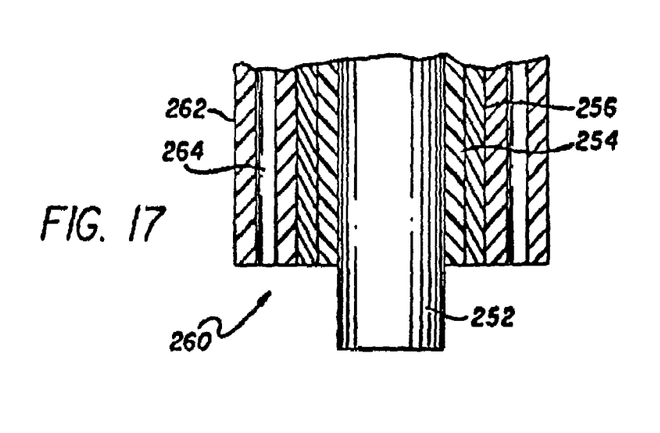
FIG. 17 is a side view of an alternate probe tip embodiment.

FIGS. 16 and 17 show alternate probe tip embodiments which have an outer electrode concentric with an inner electrode. The electrodes are coupled to the unit so that the electrodes can provide current to the cornea either simultaneously or sequentially. By way of example, it may be desirable to initially apply power to the cornea with the inner electrode and then apply power with the outer electrode, or apply power with both electrodes and then apply power with only the outer electrode. Assuming the same current value, the inner electrode will apply power with a greater current density that the outer electrode. The dual electrode probes allow the surgeon to create different thermal profiles, by varying the current densities, waveforms, etc. of the electrodes.

The probe 250 shown in FIG. 16 has an inner electrode 252 that is concentric with an intermediate layer of insulative material 254 and an outer conductive layer 256. In the preferred embodiment, the inner electrode 252 may have a diameter of 125 microns and extend from the outer layers a length of 150 microns. The outer layer 256 may have diameter of 350 microns. The inner electrode 252 may be capable of being retracted into the insulative layer 254 so that the inner electrode 252 is flush with the outer electrode 256, or may be adjusted between flush and full extension, either manually or under servo control.

FIG. 17 shows another alternate embodiment, wherein the probe 260 has an additional outer sleeve 262. The sleeve 262 has an internal passage 264 that supplies a fluid. The fluid may be a gas that stabilizes the current path to the cornea or a relatively high impedance solution (such as distilled water) which provides a coolant for the eye.

Figure 18:
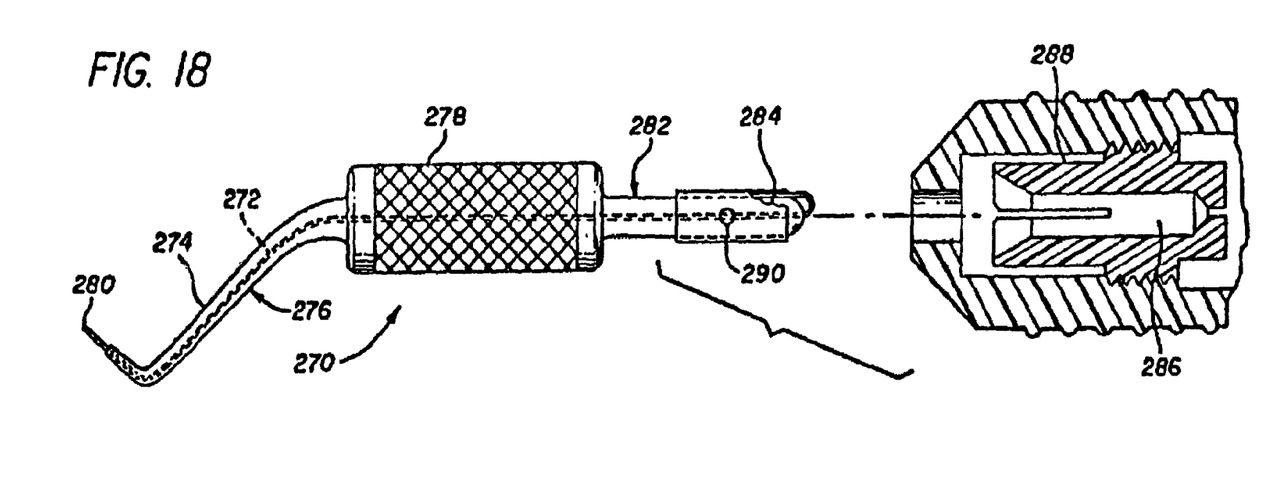
FIG. 18 is a side view of an alternate probe embodiment.

FIG. 18 shows an economical detachable probe 270 embodiment. The probe tip 270 has a conductive wire 272 that is located within a plastic outer housing 274. The probe tip 270 has a flexible section 276 that extends from a body 278, preferably at a 45° angle. The tip 280 extends from the flexible section 276, preferably at a 90° angle. Extending from the opposite end of the handle 278 is a male connector 282. The connector 282 may have a conductive sleeve 284 that is inserted into the socket 286 of a female probe connector 288. The end of the wire 272 may be pressed between the inner surface of the sleeve 284 and the outer surface of the male connector 282 to provide an electrical interconnect between the tip end 280 and the female probe connector 288. The sleeve 284 may have a detent 290 to secure the probe tip 270 to the probe connector 288. The probe tip end 280 may have distal shape configurations similar to the tips shown in FIG. 11, 13, 14, 15, 16, or 17.

Figure 19:
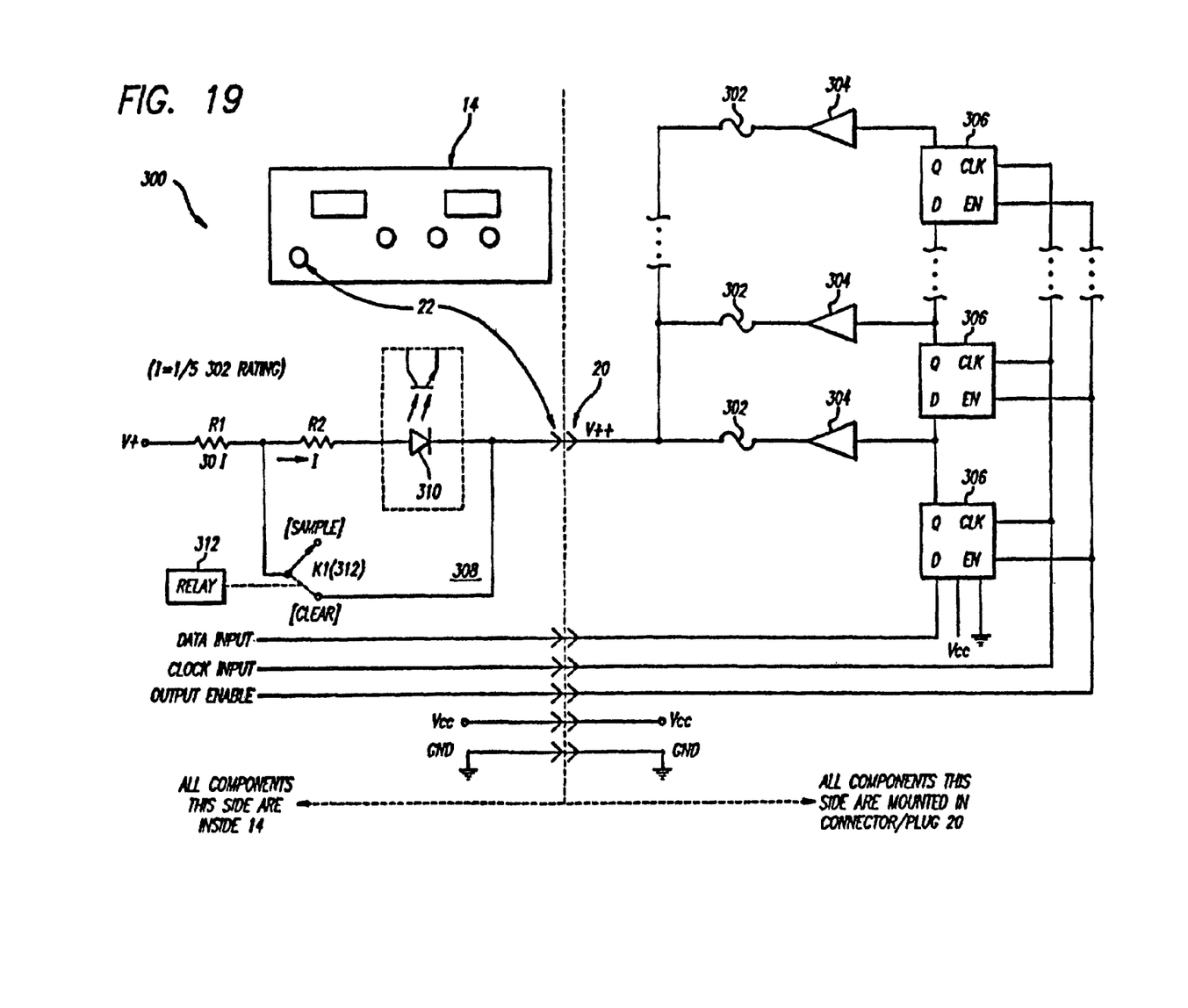
FIG. 19 is a schematic of a circuit which limits the use of a probe beyond a predetermined useful life.

FIG. 19 shows a circuit 300 that will prevent the use of the probe tip beyond a predetermined useful life. The circuit 300 has a plurality of fuses 302 that are blown each time the probe is used for a procedure. The probe is rendered inoperative when all of the fuses 302 are blown. The circuit 200 typically has 10–30 fuses 302, so that the probe can only be used 10–30 times. The circuit 300 (not shown) is preferably located on a printed circuit board (not shown) mounted to the probe. The fuses 302 may be covered with a flash inhibitor such as silica sand to prevent fuse alloy splatter/ spray when the fuses are blown.

In the preferred embodiment, the fuses 302 are connected to drivers 304 that are coupled to a plurality of serial to parallel shift registers 306. The clock pin (CLK) pins and input pin D of the first shift register are connected to the unit 14. The unit 14 initially provides an input to the first shift register and then shifts the input through the registers 306 by providing a series of pulses on the clock pin CLK. An active output of a register 306 will enable the corresponding driver 304 and select the corresponding fuse 302. The unit 14 may clock the input through the shift registers 306 in accordance with an algorithm contained in hardware or software of the unit, wherein each clock signal corresponds to the end of a procedure. By way of example, a clock signal may be generated, and a fuse blown, upon the occurrence of four shots that have a power greater than 0.16 W and a duration greater than 0.25 seconds.

The circuit 300 may have a separate sample unit 308 that is coupled to the unit 14 and the fuses 302. The sample unit 308 may have an optical coupler 310 which isolates the unit 14 from power surges, etc. or may be any voltage or current threshold/comparator circuitry known in the art. The sample unit 308 may have a relay 312 that closes a switch when the fuses 302 are to be sampled. The sample circuit 308 samples the fuses 302 to determine how many fuses 302 are not blown. The number of remaining fuses 302, which correlate to the amount of procedures that can be performed with that particular probe, may be provided by a display on the unit 14. By way of example, after sampling the fuses, the unit 14 may display the number 6 providing an indication that 6 more procedures can be performed with the probe. A 0 on the display may provide an indication that the probe must be replaced.

To sample the fuses 302, the unit 14 sets relay 312 to "sample" and clocks an input through the registers 306. If the fuse 302 is not blown when the corresponding driver 304 is enabled by the output of the register, the optical coupler 310 will be enabled. If the fuse 302 is blown the optical coupler 310 will not be enabled. The process of enabling a driver 304 and monitoring the output of optical coupler 310 is repeated for each fuse 302. The unit 14 counts the number of viable fuse links remaining to determine the remaining useful lives of the probe.

Figure 20:
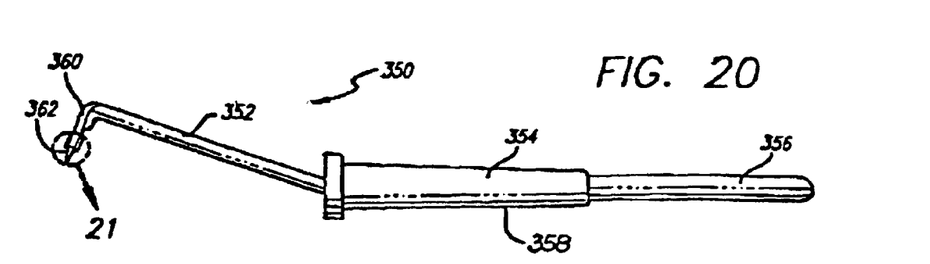
FIG. 20 is a side view of an alternate probe tip design.

FIG. 20 shows an alternate probe tip design 350. The probe tip 350 includes a spring beam 352 that extends from a handle 354. Also extending from the handle 354 is a male connector 356. The male connector 356 can be connected to the female connector of the probe shown in FIG. 18. The connector 356 allows the tip 350 to be replaced with a new unit. The handle 354 preferably has an outer plastic shell 358 that can be grasped by the surgeon. The shell 358 is constructed from a dielectric material that insulates the surgeon from the current flowing through the probe. The spring beam 352 is also typically covered with an electrically insulating material. Attached to the spring beam 352 is a tip support member 360.

Figure 21:
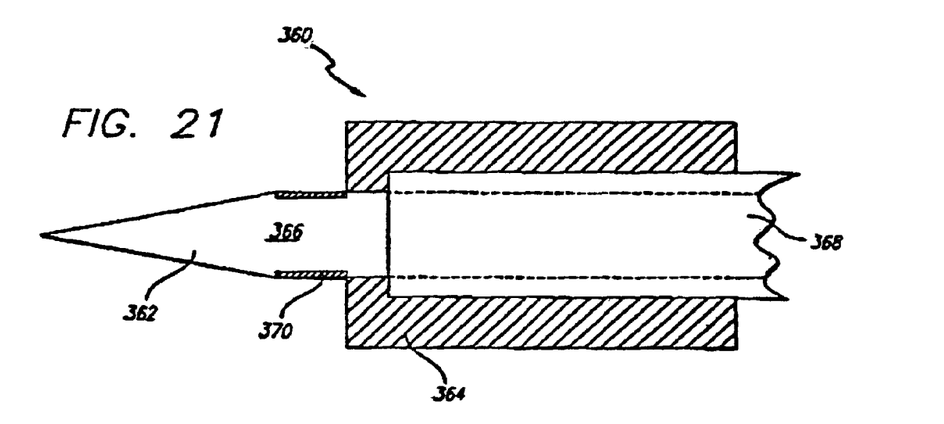
FIG. 21 is an enlarged cross-sectional view of the probe tip.

As shown in FIG. 21, the tip support 360 has a tip 362 which extends from a stop 364. The tip 362 may be the point of a wire 366 that extends to the spring beam 352. The wire 366 may be strengthened by a thickened base portion 368. The thicker wire portion 368 can be either a stepped single wire or a wire inserted into a hollow tube. There may be multiple tip supports and tips 362 attached to a single spring beam 352.

Figure 22:
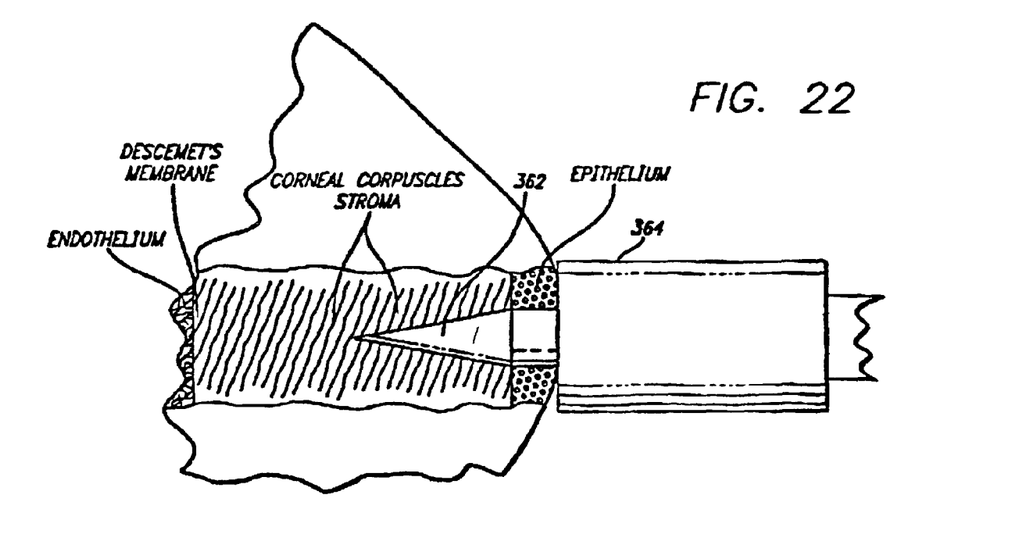
FIG. 22 is an enlarged view of the probe tip inserted into a cornea.

As shown in FIG. 22, during a procedure, the tip 362 is inserted into the cornea. The length of the tip 362 is typically 300–600 microns, preferably 400 microns, so that the electrode enters the stroma. The stop 364 limits the penetration of the tip 362. The diameter of the tip 362 is preferably 125 microns. The tip diameter is small to minimize the invasion of the eye.

The power supply provides a current to the cornea through the tip 362. The current denatures the stroma to correct the shape of the cornea. Because the tip 362 is inserted into the stroma it has been found that a power no greater than 1.2 watts for a time duration no greater than 1.0 seconds will adequately denature the corneal tissue to provide optical correction of the eye. The frequency of the power is typically between 1–20 KLHz and preferably 4 KIHz. Inserting the tip 362 into the cornea provides improved repeatability over probes placed into contact with the surface of the cornea, by reducing the variances in the electrical characteristics of the epithelium and the outer surface of the cornea.

In the preferred embodiment, the spring beam 352 is 0.90 inches long with a diameter of 0.05 inches. The tip support may be 0.25 inches long. The tip 362 may have an embedded layer of dielectric material 370 that prevents current from flowing through the epithelium. The tip 362 may be constructed from a 302 stainless steel wire that is subjected to a centerless grinding process. The grounded wire can then be exposed to a chemical milling process to create a sharp point.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A method for denaturing a cornea, comprising:
    inserting a tip into a stroma layer of a cornea;
    delivering current into the stroma layer while preventing current from flowing along a top layer of the cornea.

2. The method of claim 1, further comprising repeating the insertion of the tip and delivery of current in a circular pattern of spots having a diameter between 6–8 millimeters.

3. The method of claim 1, wherein the tip is inserted into the cornea a depth of at least 300 microns.

* * * * *